US00PP21554P2

(12) United States Plant Patent
Lyrene

(10) Patent No.: US PP21,554 P2
(45) Date of Patent: Dec. 7, 2010

(54) SOUTHERN HIGHBUSH BLUEBERRY PLANT NAMED 'FL96-43'

(50) Latin Name: ***Vaccinium corymbosum* L.**
Varietal Denomination: FL96-43

(75) Inventor: Paul M. Lyrene, Micanopy, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/587,298

(22) Filed: Oct. 5, 2009

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu
(74) *Attorney, Agent, or Firm*—Jondle & Associates, P.C.

(57) ABSTRACT

A southern highbush blueberry (*Vaccinium corymbosum*) variety particularly distinguished by having a low chilling requirement, especially for the flower buds, a vigorous, upright bush, light-blue berries with a small, dry picking scar, high firmness, and good flavor, and a very loose berry cluster.

2 Drawing Sheets

STATEMENT REGARDING FEDERALLY SPONSORED RESEARCH

The present invention was supported in part by funds from the U.S. Government. The U.S. Government therefore may have certain rights in the invention.

Genus and species: *Vaccinium corymbosum* L.
Variety denomination: 'FL96-43'.

BACKGROUND OF THE NEW PLANT

The invention relates to a new and distinct variety of southern highbush blueberry (*Vaccinium corymbosum* L.) hybrid plant named 'FL96-43.' 'FL96-43' is a southern highbush blueberry clone distinguished by its low chilling requirement, its vigorous bush, and by its large berries that ripen from mid-April through early May when grown in north Florida. Several hundred plants of 'FL96-43' have been propagated by softwood cuttings at Gainesville, Fla., and the resulting plants have all been phenotypically indistinguishable from the original plant. Contrast is made to 'Star' (U.S. Plant Pat. No. 10,675), an important variety widely planted in Florida and Georgia for early-season blueberry production. The new variety is important because it is more vigorous and has a higher yield potential than 'Star.' 'FL96-43' also has a berry that is lighter blue in color and the flower buds open after fewer hours of chilling. 'FL96-43' has been grown successfully as an evergreen plant in south-central Florida.

'FL96-43' originated as a seedling from the cross 'FL93-51' (unpatented)×'FL93-46' (unpatented) made as part of the University of Florida breeding program in a greenhouse at Gainesville, Fla. in February 1993. The seedling was first fruited in a high-density field nursery in the spring of 1995. After the second year of fruiting in the field, in the spring of 1996, 'FL96-43' was propagated by softwood cuttings, and an experimental 20-plant test plot was established as part of a variety test at Windsor, Fla. in January 1997. Based on the growth and yield of this plot, 'FL96-43' was repropagated by softwood cuttings. An experimental 30-plant plot was planted at Windsor, Fla. and another experimental 200-plant plot was planted at Archer, Fla. in February 1999. An experimental test plot of more than 100 plants was established at Haines City, Fla. in 2002. These plots have been observed during flowering and ripening each year, and no mutations or off-type plants have been observed.

SUMMARY OF THE INVENTION

The following are the most outstanding and distinguishing characteristics of this new cultivar when grown under normal horticultural practices in Florida.

1. A low chilling requirement, especially for the flower buds;
2. A vigorous, upright bush;
3. Light-blue berries with a small, dry picking scar, high firmness, and good flavor; and
4. A very loose berry cluster.

DESCRIPTION OF THE PHOTOGRAPHS

The color chart used in this specification is "The Pantone Book of Color" (by Leatrice Eiseman and Lawrence Herbert, Harry N. Abrams, Inc., Publishers, New York, 1990). Where colors in the drawings differ from the Pantone color designations in the descriptions, the Pantone color designations are accurate. The colors shown are as true as can be reasonably obtained by conventional photographic procedures.

Figure 1:
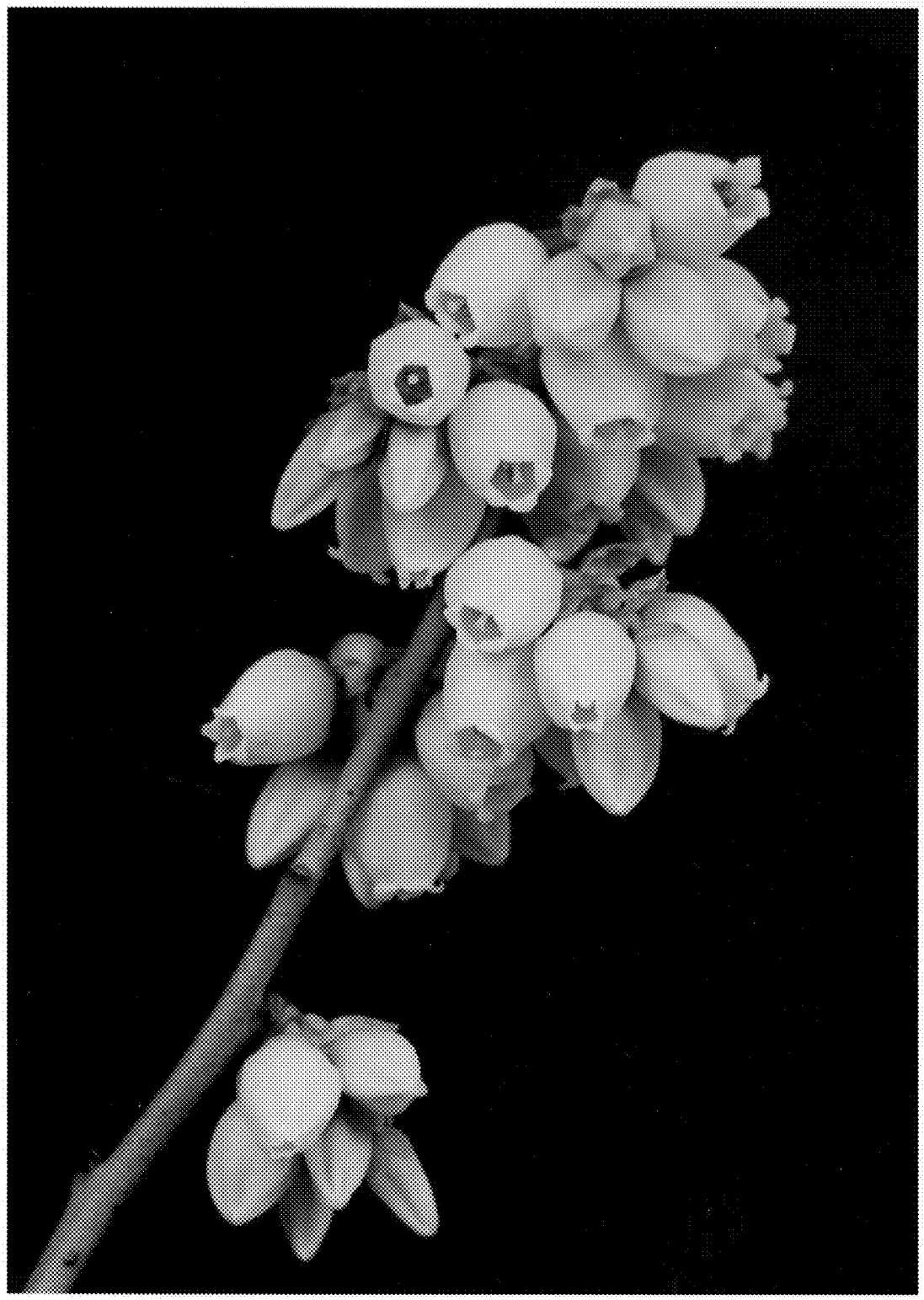
FIG. 1 shows several clusters of opening flowers during the early stages of flowering in February.
Figure 2:
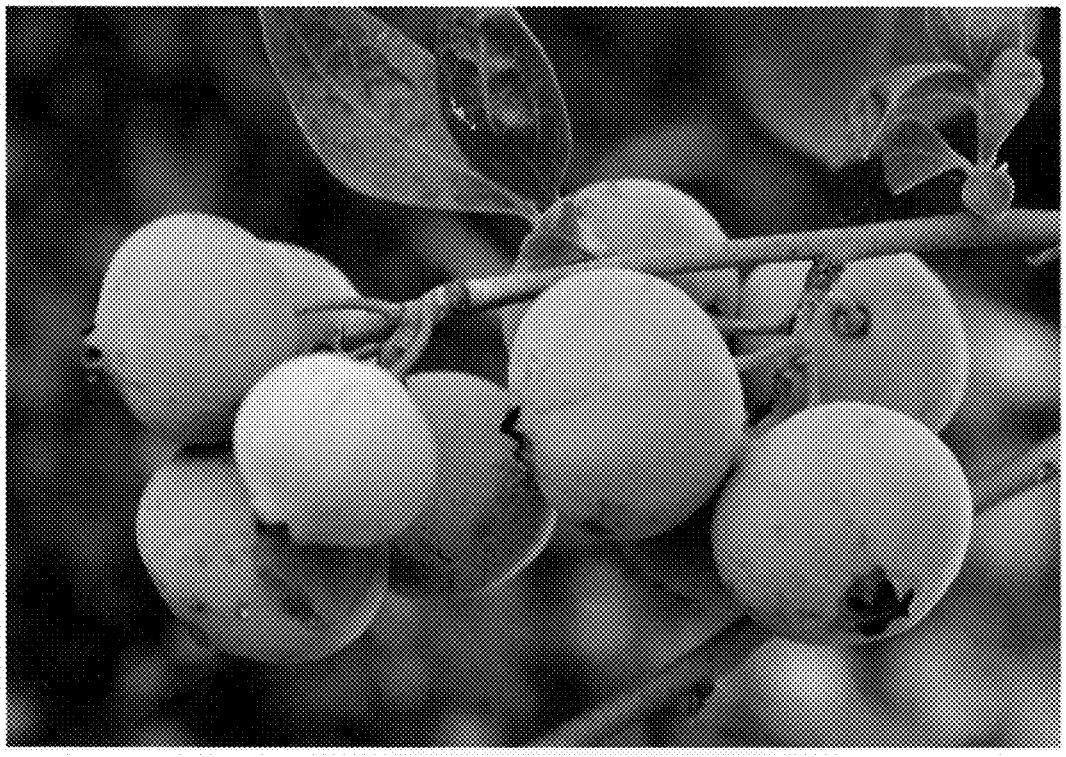
FIG. 2 shows several clusters of berries ripening in the field.
Figure 3:
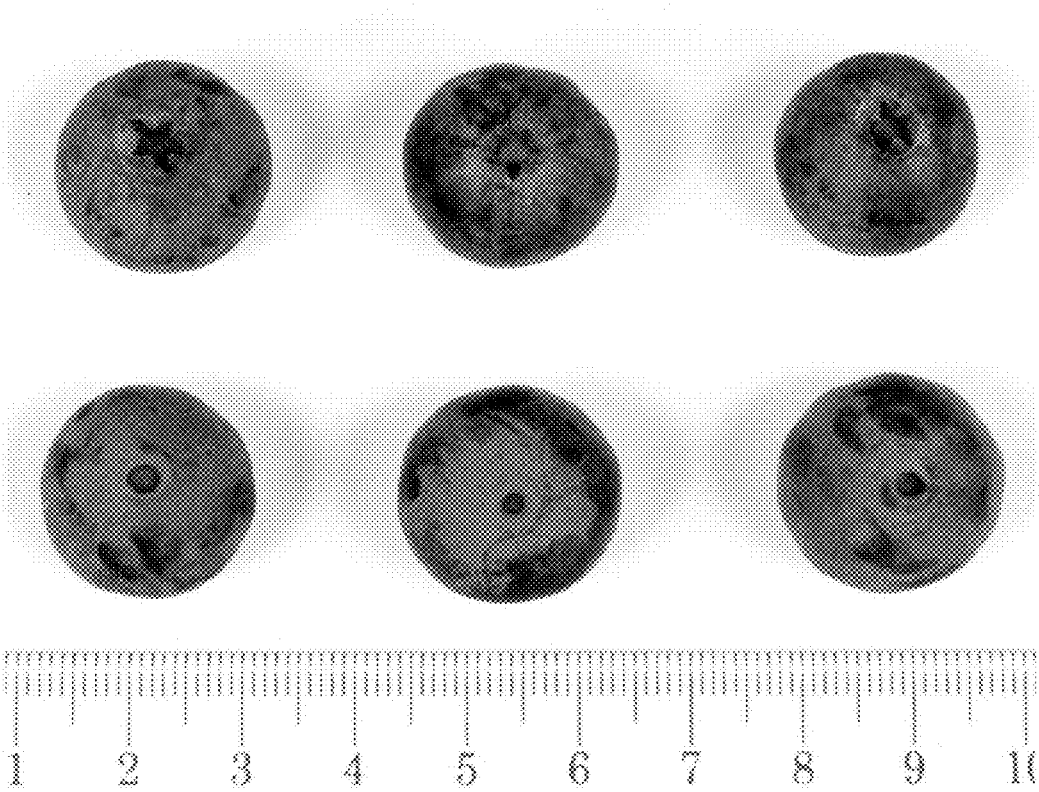

FIG. 3 shows berries at close range. The small, dry picking scars and small calyx aperture are visible. The berries are normally much lighter in color than indicated by FIG. 3, in which the surface wax has been abraded by handling the berries.

DESCRIPTION OF THE NEW CULTIVAR

The following detailed description sets forth the distinctive characteristics of 'FL96-43.' The data which define these characteristics were collected from asexual reproductions carried out in Florida. The plant history was taken on 10-year-old plants. The following descriptions relate to plants grown in the field near Archer in northeast Florida. Color designations are from "The Pantone Book of Color" (by Leatrice Eiseman and Lawrence Herbert, Harry N. Abrams, Inc., Publishers, New York, 1990). Where the Pantone color designations differ from the colors in the Drawings, the Pantone colors are accurate.

DETAILED BOTANICAL DESCRIPTION

Classification:

*Family.*—Ericaceae.

*Botanical.*—*Vaccinium corymbosum* L.

*Common name.*—Southern Highbush Blueberry.

Parentage:

*Female parent.*—'FL93-51,' a proprietary southern highbush blueberry plant (unpatented).

*Male parent.*—'FL93-46,' a proprietary southern highbush blueberry plant (unpatented).

Market class: 'FL96-43' produces southern highbush blueberries suitable for both the fresh and processed fruit markets.

Plant:

*General.*—Bush characteristics were taken from a plot of two hundred 10-year-old plants growing in a test plot in a commercial field near Archer in northeast Florida.

*Plant height.*—2.0 m.

*Canopy* (*diameter measured at widest part of the bush*) .—2.5 m.

*Plant vigor.*—High; more vigorous than 'Star'.

*Growth habit.*—Upright.

*Flower bud density* (*number*) *along flowering twigs in January.*—High.

*Twigginess.*—Medium.

*Tendency toward evergreenness.*—Medium to high.

*Productivity.*—In northeast Florida, 'FL96-43' produces 5 to 8 pounds of berries per bush on plants 3 years old or older.

*Chilling requirement.*—200 hours below 7° C.

*Cold hardiness.*—Flowers and fruit are hardy to −3° C.; the plant is hardy to −15° C. during winter dormancy.

*Ease of propagation.*—'FL96-43' is easy to propagate from softwood cuttings; the plants survive and grow well in nursery beds.

Trunk and branches:

*Suckering tendency.*—Medium; 10-year-old plants have ten major canes rising from a crown 30 cm in diameter.

*Surface texture* (*of strong, 6-month-old shoots observed in June*).—Smooth.

*Surface texture* (*of 3-year-old and older wood*).—Rough due to exfoliation and production of vertical cracks.

*Color of new twigs observed in June in the field.*—"Green Banana," Pantone 14-0434.

*Color of 3-year-old, rough-textured canes.*—"Birch," Pantone 13-0905.

*Internode length on strong, upright shoots measured in June.*—Averages about 1.8 cm.

Leaves:

*Length, mean* (*including petiole, from tip of petiole to end of blade*).—5.6 cm.

*Width, mean* (*at widest point*).—2.8 cm.

*Shape.*—Ovate, terminating in a very short dew tip, 0.05 cm long, which is visible with a 15× microscope.

*Margin.*—Entire except for 5 to 10 sessile glands on each side, visible at 20×.

*Color.*—Upper surface: "Chive," Pantone 19-0323. Lower surface: "Stone Green," Pantone 17-0123.

*Pubescence on upper surface of leaves.*—Sparse distribution of short, curled, white hairs along midrib.

*Pubescence on the lower surface of leaves.*—Absent.

*Pubescence on margins.*—Absent.

*Relative time of leafing versus flowering.*—In commercial fields in north Florida, wherein the plant is sprayed with hydrogen cyanamide in midwinter, 'FL96-43' normally flowers before significant leafing begins.

Flowers:

*Arrangement.*—Flowers are arranged alternately along a short, leafless, deciduous branch.

*Fragrance.*—Has a light rose fragrance.

*Shape.*—Urceolate.

*Flowering period.*—Mean date of 50% open flowers in Windsor, Fla. is February 5; averages ten days before 'Star'.

*Cluster* (*tight, medium, loose*).—Loose.

*Average number of flowers per cluster.*—5.

*Pedicel.*—Length at time of anthesis: 0.9 cm. Color: "Fuchsia Red," Pantone 18-2328.

*Peduncle.*—Length at time of anthesis: Highly variable; median is 1.2 cm. Color: "Fuchsia Red," Pantone 18-2328.

*Calyx.*—Surface texture: Smooth. Color at anthesis: "Cameo Green," Pantone 14-6312.

*Corolla.*—Diameter of tube (at widest point): 0.8 cm. Aperture diameter: 0.2 cm to 0.3 cm. Surface texture: Smooth. Color at anthesis: White to "Chalk," Pantone 12-2902. Length (from pedicel attachment point to corolla tip excluding the pedicel): Median is 1.1 cm.

Reproductive organs:

*Style length* (*top of ovary to stigma tip*).—0.9 cm.

*Location of tip of stigma relative to lip of the corolla.*—Co-equal.

*Pollen.*—Abundance of shed: Medium. Staining with 2% acetocarmine (a measure of potential pollen fertility): Over 99%. Color of dried pollen: "Winter White," Pantone 11-0507.

*Self fruitfulness.*—Low. Planting in field configurations that promote cross pollination with other southern highbush clones is recommended for all southern highbush blueberry plants in Florida.

Fruit:

*Mean date of first commercial harvest* (*25% of berries ripe*).—April 14.

*Mean date of mid-harvest.*—April 28.

*Mean date of last harvest.*—May 10.

*Diameter of calyx aperture on mature berry.*—0.3 cm.

*Size and shape of calyx lobes on mature berry.*—Very small lobes, irregular but occasionally making a 5-point star. Very small calyx dish.

*Pedicel length on ripe berry.*—Median is 0.9 cm.

*Peduncle length on ripe berry.*—Variable; median is 0.8 cm.

*Detachment force for ripe berries.*—Medium.

*Number of berries per cluster.*—Median is 6.

Berry:

*Cluster* (*tight, medium, or loose*).—Loose.

*Weight* (*on well-pruned plants*).—2.4 g per berry compared to 2.0 g per berry for 'Star'.

*Height.*—1.5 cm.

*Width.*—1.6 cm.

*Shape.*—Globose; only very slightly flattened pole to pole.

*Surface color of mature berries while on the plant.*—"Quarry," Pantone 15-4305.

*Surface color of ripe berry after polishing.*—Shiny black.

*Immature berry color, with bloom*—"Spray", Pantone 13-6007 with blush of "Light Lilac", Pantone 12-2903 where exposed to sunlight.

*Surface wax.*—Abundant surface wax which makes the exterior color of the ripe berry lighter blue. The wax on this cultivar has above-normal resistance to abrasion.

*Pedicel scar.*—Small and dry.

*Firmness.*—High.

*Flavor.*—Sweet, with some acid; berry sweet when it first becomes blue.

*Texture.*—Good; small seeds, thin skinned.

Seeds:

*Color of dried seeds.*—"Glazed Ginger," Pantone 18-1154.

*Weight of well-developed dried seed.*—0.5 mg per seed.

*Length of well-developed dried seed.*—0.15 cm.

Resistance to diseases, insects, and mites: 'FL96-43' has grown vigorously and shows medium to good bush survival in the field. It appears to have above-average resistance to root rot (*Phytophthora cinnamomi*) and average resistance stem blight (*Botryosphaeria* spp.). The plants have shown no signs of cane canker (*Botryosphaeria corticis*) susceptibility in the field. The fungal leaf spots that are common on highbush blueberries grown in Florida are easily controlled by approved fungicides.

COMPARISON WITH PARENTAL AND KNOWN CULTIVARS

'FL96-43' differs from the proprietary female (seed) parent 'FL93-51' (unpatented) in that 'FL96-43' has a more vigorous bush and a lighter berry color, as contrasted with the very dark berry color of 'FL93-51'.

'FL96-43' differs from the male (pollen) parent 'FL93-46' (unpatented) in that 'FL96-43' has a larger berry with a smaller picking scar and higher berry firmness than 'FL93-46'.

'FL96-43' differs from the commercial variety 'Star' (U.S. Plant Pat. No. 10,675), an important variety widely planted in Florida and Georgia for early-season blueberry production, in that 'FL96-43' is more vigorous and upright with a higher yield potential than 'Star'.

I claim:

1. A new and distinct variety of southern highbush blueberry plant as shown and described herein.

* * * * *